US006417187B2

(12) United States Patent
Hegde et al.

(10) Patent No.: US 6,417,187 B2
(45) Date of Patent: Jul. 9, 2002

(54) 1,2,4-TRIAZOLE BASED COMPOUNDS THAT CAN BE USED AS INSECTICIDES OR ACARICIDES AND PROCESSES

(75) Inventors: Vidyadhar Babu Hegde; Scott Jerome Bis, both of Carmel, IN (US); Emilie Chassat Heo, Houston, TX (US); Christopher Thomas Hamilton, Midland, MI (US); Peter Lee Johnson, Indianapolis, IN (US); Laura Lee Karr, Lebanon, IN (US); Timothy Patrick Martin, Indianapolis, IN (US); Paul Allen Neese, Tucson, AZ (US); Nailah Orr; Francis Eugene Tisdell, both of Carmel, IN (US); Maurice Chee Hoong Yap, Zionsville; Yuanming Zhu, Carmel, both of IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/834,845

(22) Filed: Apr. 13, 2001

Related U.S. Application Data

(60) Provisional application No. 60/197,179, filed on Apr. 14, 2000.

(51) Int. Cl.[7] .................... C07D 413/14; C07D 249/08; A01N 43/82
(52) U.S. Cl. ............................. 514/236.2; 548/266.2; 548/110; 514/340; 514/383; 546/272.4; 544/112
(58) Field of Search .................. 548/266.2; 546/272.4; 514/383, 340, 236.2; 544/112; 504/225

(56) References Cited

U.S. PATENT DOCUMENTS 5,482,951 A   1/1996   Ozaki et al. ................. 514/340

FOREIGN PATENT DOCUMENTS

| EP | 572142 | 1/1993 |
| JP | 8092224 | 4/1993 |
| JP | 08283261 | 10/1996 |

OTHER PUBLICATIONS

Akerblom, Eva B. and Campbell, Dag E.S., J. Med. Chem. "Nitrofuryltriazole Derivatives as Potential Urinary Tract Antibacterial Agents" 1973, 16(4), 312.
Akerblom, Eva B., J. Med. Chem. "Nitrofurans with High Renal Excretion" 1974, 17(7), 756.
Benjamin, Louis E. and Snyder, Harry R., Jr. "Nitrofuryl Heterocycles. XIII(1). N–Methyl–3–methylthio–5–(5–nitro–2–furanyl)–1H–1,2, 4–traizoles" J. Hetercyclic Chem. 1976, 13, 1115.

Primary Examiner—Joseph K. McKane
Assistant Examiner—Kamal Saeed
(74) Attorney, Agent, or Firm—Carl D. Corvin

(57) ABSTRACT

3-(Substituted aryl)-5-{substituted aryl-(alkynyl-aryl)}-[1,2,4]- triazole compounds are useful as insecticides and acaricides. New synthetic procedures and intermediates for preparing the compounds, pesticide compositions containing the compounds, and methods of controlling insects and mites using the compounds are also provided.

27 Claims, No Drawings

1,2,4-TRIAZOLE BASED COMPOUNDS THAT CAN BE USED AS INSECTICIDES OR ACARICIDES AND PROCESSES

PRIORITY

This application claims a priority from U.S. Provisional Application 60/197,179 filed Apr. 14, 2000.

FIELD OF THE INVENTION

This invention provides new compounds that are useful as insecticides and acaricides, new synthetic procedures and intermediates for preparing the compounds, pesticide compositions containing the compounds, and methods of controlling insects and mites using the compounds.

BACKGROUND OF THE INVENTION

There is an acute need for new insecticides and acaricides. Insects and mites are developing resistance to the insecticides and acaricides in current use. At least 400 species of arthropods are resistant to one or more insecticides. The development of resistance to some of the older insecticides, such as DDT, the carbamates, and the organophosphates, is well known. But resistance has even developed to some of the newer pyrethroid insecticides and acaricides. Therefore a need exists for new insecticides and acaricides, and particularly for compounds that have new or atypical modes of action.

A number of 3,5-diphenyl-1H-1,2,4-triazole derivatives have been described in the literature as having acaricidal activity (U.S. Pat. No. 5,482,951; JP 8092224, EP572142, JP 08283261). Nitro furanyl triazoles are described by L. E. Benjamin and H. R. Snyder as antimicrobials (*J Heterocyclic Chem.* 1976, 13, 1115) and by others as antibacterials (*J Med. Chem.* 1973, 16(4), 312; *J Med. Chem.* 1974, 17(7), 756). The present invention provides novel compounds with broad spectrum activity against mites and insects.

SUMMARY OF THE INVENTION

This invention provides novel compounds especially useful for the control of insects and mites.

More specifically, the invention provides novel insecticidally active compounds of the formula (1)

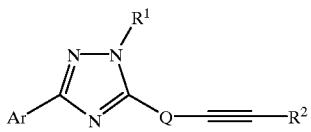

(1)

wherein

Ar is phenyl, substituted phenyl, pyridyl, substituted pyridyl, or lower alkyl;

$R^1$ is lower alkyl, cycloalkyl, phenyl, or substituted phenyl;

Q is thienyl, substituted thienyl, phenyl, substituted phenyl, pyridyl, or substituted pyridyl;

$R^2$ is selected from H, lower alkyl, lower alkenyl, pyridyl, substituted pyridyl, pyrimidyl, substituted pyrimidyl, isoxazolyl, substituted isoxazolyl, naphthyl, substituted naphthyl, phenyl, substituted phenyl, thienyl, substituted thienyl, —$(CH_2)_m R^3$, —CH=$CHR^3$, —C≡$CR^3$, —$CH_2OR^3$, —$CH_2SR^3$, —$CH_2NR^3R^3$, —$OCH_2R^3$, —$SCH_2R^3$,—

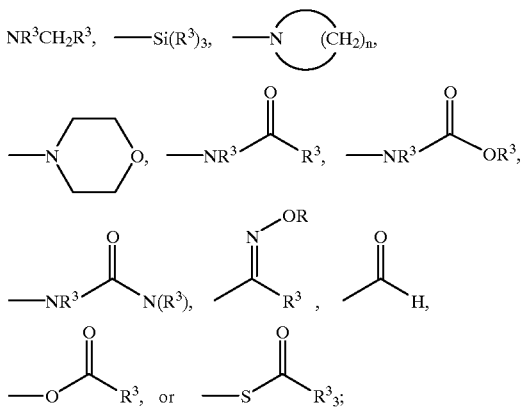

$R^3$ is H, lower alkyl, haloalkyl, lower alkenyl, lower alkynyl, phenyl, or substituted phenyl;

m is 1 or 2;

n is an integer from 2 to 6; or a phytologically acceptable acid addition salt thereof.

Preferred compounds of formula (1) include the following classes:

(1) Compounds of formula (1) wherein Ar is a group of the formula

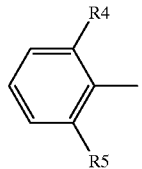

wherein $R^4$ and $R^5$ are independently H, Cl, F, methyl, halomethyl, methoxy, or halomethoxy.

(2) Compounds of formula (1) wherein Ar is a group of the formula

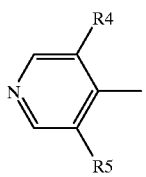

wherein $R^4$ and $R^5$ are independently H, Cl, F, methyl, halomethyl, methoxy, or halomethoxy.

(3) Compounds of class (1) and (2) wherein $R^4$ and $R^5$ are independently F or Cl.

(4) Compounds of class (1) and (2) wherein $R^4$ and $R^5$ are both F.

(5) Compounds of class (1) and (2) wherein $R^4$ and $R^5$ are both Cl.

(6) Compounds of class (1) and (2) wherein $R^4$ is F and $R^5$ is Cl.

(7) Compounds of formula (1), and particularly compounds of class (1), (2), (3), (4), (5) or (6) as defined above, wherein Q is a substituted thiophene.

(8) Compounds of formula (1), and particularly compounds of class (1), (2), (3), (4), (5) or (6) as defined above, wherein Q is a substituted phenyl.

(9) Compounds of formula (1), and particularly compounds of any one of classes (1) through (8) as defined above, wherein $R^2$ is methyl.

(10) Compounds of formula (1), and particularly compounds of any one of classes (1) through (9) as defined above, wherein $R^2$ is a phenyl or substituted phenyl.
(11) Compounds of formula (1), and particularly compounds of any one of classes (1) through (9) as defined above, wherein $R^2$ is a thiophene or substituted thiophene.

The invention also provides new processes and intermediates for preparing compounds of formula (1) as well as new compositions and methods of use, which will be described in detail hereinafter.

DETAILED DESCRIPTION OF THE INVENTION

Throughout this document, all temperatures are given in degrees Celsius, and all percentages are weight percentages unless otherwise stated.

The term "lower alkyl" refers to ($C_1$–$C_6$) straight hydrocarbon chains and ($C_3$–$C_6$) branched and cyclic hydrocarbon groups.

The terms "lower alkenyl" and "lower alkynyl" refer to ($C_2$–$C_6$) straight hydrocarbon chains and ($C_3$–$C_6$) branched hydrocarbon groups containing at least one double or triple bond, respectively.

The term "lower alkoxy" refers to —O—lower alkyl.

The terms "halomethyl", "haloalkyl", and "haloalkenyl" refer to methyl, lower alkyl, and lower alkenyl groups substituted with one or more halo atoms.

The terms "halomethoxy" and "haloalkoxy" refer to methoxy and lower alkoxy groups substituted with one or more halo atoms.

The term "alkoxyalkyl" refers to a lower alkyl group substituted with a lower alkoxy group.

The term "alkoxyalkoxy" refers to a lower alkoxy group substituted with a lower alkoxy group.

The terms "substituted naphthyl", "substituted thienyl," "substituted pyrimidyl," "substituted pyrazolyl," "substituted pyridyl," and "substituted isoxazolyl" refer to the ring system substituted with one or more groups independently selected from halo, halo ($C_1$–$C_4$) alkyl, CN, $NO_2$, ($C_1$–$C_4$) alkyl, ($C_3$–$C_4$) branched alkyl, phenyl, ($C_1$–$C_4$) alkoxy, or halo ($C_1$–$C_4$) alkoxy.

The term "substituted phenyl" refers to a phenyl group substituted with one or more groups independently selected from halo, ($C_1$–$C_{10}$) alkyl, branched ($C_3$–$C_6$) alkyl, halo ($C_1$–$C_7$) alkyl, hydroxy ($C_1$–$C_7$) alkyl, ($C_1$–$C_7$) alkoxy, halo ($C_1$–$C_7$) alkoxy, phenoxy, phenyl, $NO_2$, OH, CN, ($C_1$–$C_4$) alkanoyl, benzoyl, ($C_1$–$C_4$) alkanoyloxy, ($C_1$–$C_4$) alkoxycarbonyl, phenoxycarbonyl, or benzoyloxy.

Unless otherwise indicated, when it is stated that a group may be substituted with one or more substituents selected from an identified class, it is intended that the substituents may be independently selected from the class.

Synthesis

Compounds of formula (1) can be prepared by the methods illustrated in Scheme 1:

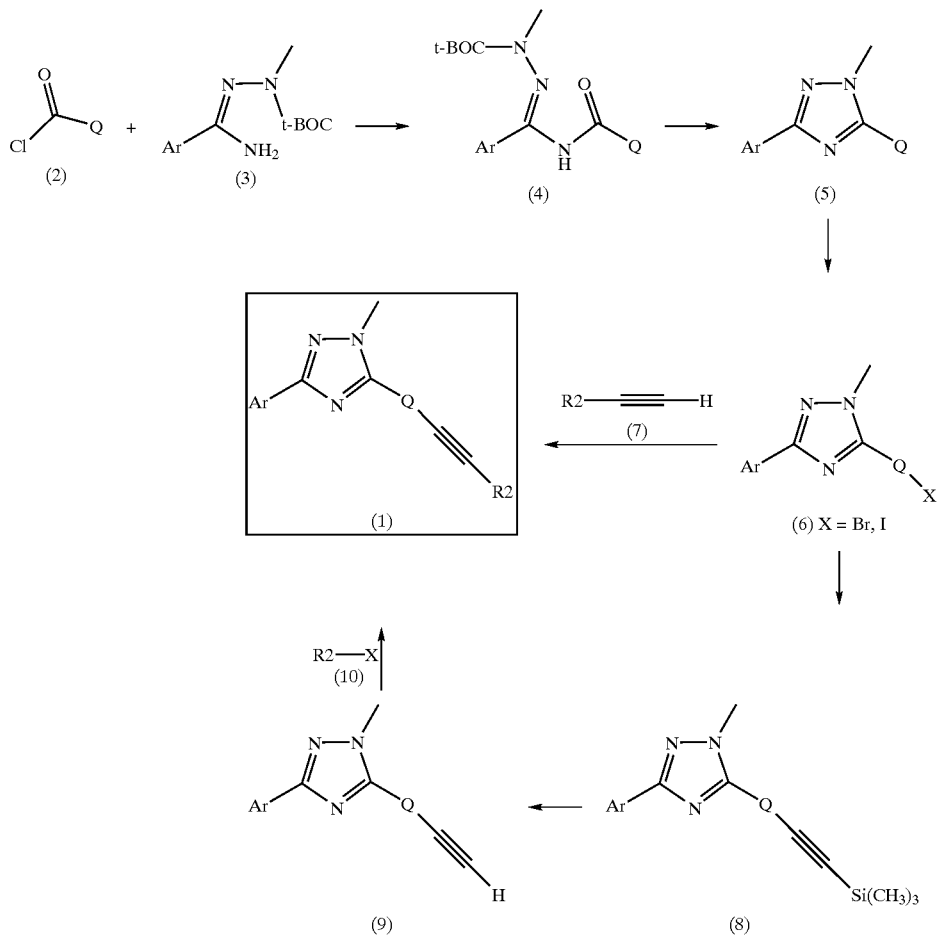

wherein Ar is phenyl or substituted phenyl, Q, and $R^2$ are defined as in formula (1) above. The sequence shown in Scheme 1 involves the coupling of acid chlorides of formula (2) with the amidrazone of formula (3). Preparation 1, hereinafter, illustrates preparation of an amidrazone of formula (3). The base used in the coupling could be any organic or inorganic base. Acid chlorides of formula (2) are prepared from corresponding carboxylic acids of formula (11)

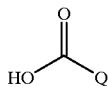
(11)

which are either commercially available or are readily made through known procedures. Examples 1 and 2, hereinafter, illustrate the coupling and cyclization utilizing the amidrazone of formula (3) to produce a triazole product of formula (1).

Preparation 1

The following steps illustrate preparation of the amidrazone of formula (3a)

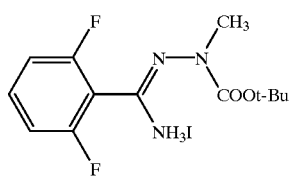
(3a)

A. 2,6-difluorobenzenethioamide

Into a 3 L three necked round bottom flask equipped with a mechanical stirrer, dry ice condenser, dropping funnel, and outlet to a trap filled with bleach was added pyridine (550 mL), 2,6-difluorobenzonitrile (208 g, 1.50 mol), triethylamine (202 g, 279 mL, 2.0 mol), and sodium sulfide hydrate (521 g, 2.17 mol-broken into pieces small enough to fit into the flask). The temperature of the stirred mixture was lowered to approximately 5° C. and to the slurry was added dropwise concentrated hydrochloric acid (143 g, 288 mL, 3.99 mol). An exotherm was noted and the rate of addition of the hydrochloric acid was such that the temperature of the reaction mixture did not exceed 25° C. for a total addition time of 75 min. The cooling bath was removed and the slurry was allowed to warm to RT and to stir over night. The mixture was poured into water (2 L) and was extracted with ether (3×500 mL). The ether layer was washed with dilute sulfuric acid, water, brine, dried ($MgSO_4$), and the solvent removed in vacuo to give 232 grams of crude product. The starting material was removed from the product via kugelrohr distillation to give 197 g (76%) of 2,6-difluorobenzenethioamide. This material was used without further purification.

B. S-methylthio-2,6-difluorobenzamidinium iodide

Into a 3 L three necked flask equipped with a mechanical stirrer and dropping funnel was added acetone (1150 mL) and 2,6-difluorobenzenethioamide (197 g, 1.14 mol). The temperature of the stirred solution was lowered to approximately 5° C. and iodomethane (161 g, 70.6 mL, 1.14 mol) was added dropwise. The ice bath was removed and the slurry was allowed to stir over night. The resulting yellow solids were removed via filtration and washed with ether to obtain 223 grams. An additional portion of material was obtained from the filtrate by removal of the solvent in vacuo.

Ether was added to the residue and the resulting solids removed via filtration to obtain an additional 57 grams of material. The combined solids totaled 280 g (77.9% yield) of S-methylthio-2,6-difluoro-benzimidinium iodide: mp 168–169° C.; $^1$H NMR (DMSO-$d_6$) δ7.7 (m, 1H), 7.4 (m, 2H), 2.7 (s, 3H).

C. N-tert-butoxycarbonyl-N-methylhydrazine

Into a 1 L three necked round bottom flask equipped with a mechanical stirrer and dropping funnel was added methyl hydrazine (42.2 g, 0.916 mol) and THF (100 mL). The temperature of the mixture was cooled to 5° C. and a solution of di-tert-butyl dicarbonate (100 g, 0.458 mol) dissolved in THF (150 mL) was added dropwise. The cooling bath was removed and the mixture was stirred at RT overnight. The liquid was decanted from a gummy precipitate and the solvent removed in vacuo to give approximately 70 grams of a clear liquid. The gummy precipitate was partitioned between methylene chloride and water. The methylene chloride was washed with brine, dried ($Na_2SO_4$) and the solvent removed in vacuo. The resulting residue was combined with that from the previous evaporation and distilled at approximately 20 mm Hg (bp 77–78° C.) to give 40.2 g (60% yield) of N-tert-butoxycarbonyl-N-methylhydrazine: $^1$H NMR (CDCl$_3$) 6 4.1 (bs, 2H), 3.05 (s, 3H), 1.5 (s, 9H).

D. Amidrazone of formula (3a)

Into a 1 L round bottom flask equipped with a mechanical stirrer, dropping funnel, and outlet to a trap filled with bleach, was added S-methyl-2,6-difluorobenziminium iodide (63.8 g, 0.202 mol) and methanol (180 mL). To the stirred solution was added dropwise N-tert-butoxycarbonyl-N-methylhydrazine (29.6 g. 0.202 mol). The solution was allowed to stir overnight and the methanol was removed in vacuo. The residue was triturated with ether and the solids removed via filtration to give 66.3 grams (79.0% yield) of the amidrazone of formula (3a): mp 172–173° C. (dec); $^1$H NMR (DMSO-$d_6$) δ12.3 (s, b, 1H), 10.4 (d, b, 2H), 7.9 (m, 1H), 7.4 (m, 2H), 3.1 (s, 3H), 1.5 (s, 9H).

EXAMPLE 1

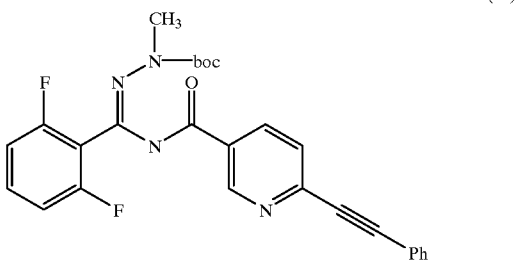
(4a)

A mixture of the t-Boc protected amidrazone (3a) (0.86 g, 3.0 mmol), the 6-Phenylethynylnicotinic acid (0.67 g, 3.0 mmol) and dicyclohexylcarbodiimide (0.62 g, 3.0 mmol) in 10 mL of $CH_2Cl_2$ was treated with a catalytic amount of 4-N,N-dimethylaminopyridine. The resultant mixture was allowed to stir at room temperature, under $N_2$. After 40 hours the reaction mixture was filtered through a plug of Celite, washing with $CH_2Cl_2$. The filtrate was concentrated in vacuo to give 1.75 g of a yellow oil. This was chromatographed on silica gel (MPLC), eluting with 65% hexanes/35% ethyl acetate. Isolation of the major product gave 0.54 g (37% yield) of the desired product as a yellow oil: $^1$H NMR (CDCl$_3$) δ10.2 (br, 1H), 9.09 (dd, 1H, J =0.6, 1.8 Hz), 8.14 (dd, 11H, J =2.4, 8.3 Hz), 7.63–7.60 (m, 3H), 7.40–7.38 (m, 4H), 6.98–6.93 (m, 2H), 3.29 (s, 3H), 1.49 (s, 9H).

EXAMPLE 2

1-Methyl-3-(2,6-difluorophenyl)-5-(6-ethynylphenyl-3-pyridinyl)-1,2,4-Triazole (1a)

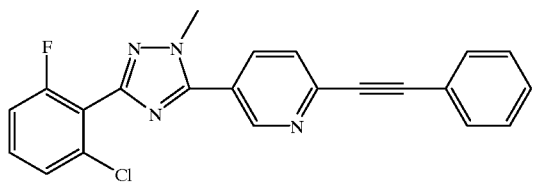

(1a)

A mixture of the t-Boc protected amidrazone (4a) and 5 mL of trifluoroacetic acid was allowed to stir at room temperature. After stirring for three days TLC analysis showed that all of the starting material had been consumed. The reaction mixture was poured into $H_2O$ (25 mL) and extracted with ethyl acetate (3×25 mL). The combined organic extracts were washed with $H_2O$ (2×25 mL), saturated NaCl (1×25 mL), dried ($MgSO_4$), filtered and concentrated to give 0.63 g of a dark yellow oil. This was chromatographed on silica gel (MPLC), eluting with 70% hexane/30% ethyl acetate. Isolation of the major product gave 0.208 g (56% yield) of the desired product as a light tan solid: mp 137–138° C.; $^1$H NMR ($CDCl_3$) δ9.02 (dd, 1H, J=0.9, 2.6 Hz), 8.14 (dd, 1H, J=2.1, 8.4 Hz), 7.70 (dd, 1H, J=0.9, 8.1 Hz), 7.65–7.62 (m, 2H), 7.42–7.37 (m, 4H), 7.06–7.00 (m, 2H), 5.15 (s, 3H). Another route to intermediates of formula (5) is shown in Scheme 2, wherein Ar, Q, and $R^1$ are as defined in formula (1).

Scheme 2

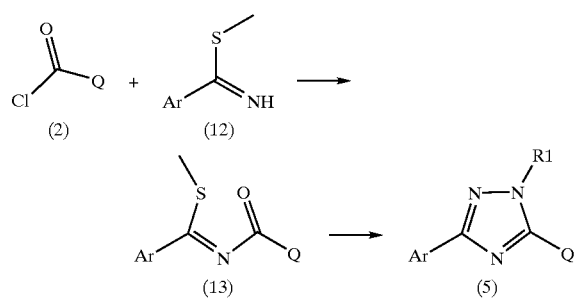

Aryl acyl(thio)imidates of type (12) are known in the literature and can be used as their acid addition salt. In this case, tetrafluoroboric acid, hydrogen chloride, hydrogen bromide, hydrogen iodide, or the like, may be used. Aryl acylimidates are available through the nitrile (*J Org. Chem.* 1968, 33, 1679 and U.S. Pat. No. 4,025,504). Methyl thioimidate of formula (12) are prepared from corresponding arylnitriles of formula (14) where $R^4$ and $R^5$ are as defined in formula 1 above and X is carbon or nitrogen,

Scheme 3

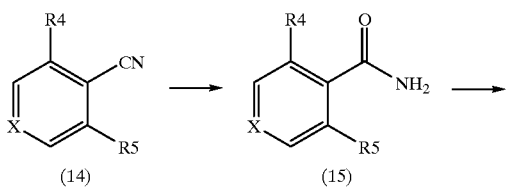

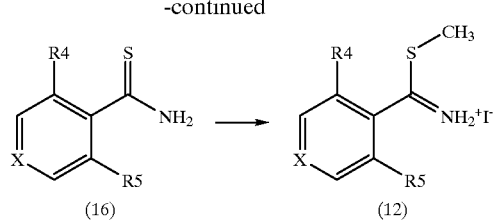

which are either commercially available or are readily made through known procedures as depicted in Scheme 3 and as illustrated hereinafter in Preparation 2. Thioimidates are readily available through alkylation of the corresponding thioamides which themselves are commercially available or can be made from the amide (Phosphorous Sulfur (1985), 25(3), 297–305) or nitrile (*Chem.-Ztg.* 1980, 104, 365; *J Chem. Soc.* 1952, 742; Can. *J Chem.* 1985, 63, 3075). Reaction of the acid chloride of formula (2) and the imidate (12) to give adduct (13) can be accomplished in any inert solvent with any organic or inorganic base. Reaction of compounds such as (13) with alkyl or aryl substituted hydrazine gives the triazole intermediate (5) in good yield with a high degree of regiospecificity. Preparation 3, hereinafter, illustrate the preparation of a thioamide of formula (13) using the above described procedure. Preparations 4 and 5, hereinafter, illustrate the synthesis of a triazole of formula (5) using the procedure involving the addition of a substituted hydrazine to the thioamide of formula (13).

Preparation 2

The following steps illustrate preparation of S-methylthio-3,5-dichloro-4-pyridylimidinium iodide (12a)

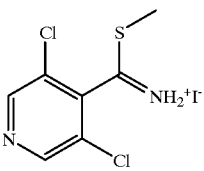

(12a)

A. 3,5-dichloro-4-pyridinethioamide (16a)

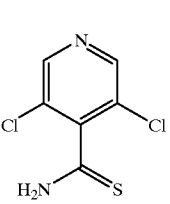

(16a)

Into a 3000-mL three-necked round bottom flask equipped with a condenser, mechanical stirrer under an atmosphere of nitrogen was added pyridine (1500 mL), then 3,5-dichloro-4-pyridine-carboxamide (92.9 g, 0.486 mol) which dissolved, and tetraphosphorus decasulfide (237 g, 0.535 mol), which had almost dissolved then a bright yellow precipitate formed and an exotherm heated the mixture to 60° C. The slurry was allowed to stir for 1 h (temperature had dropped to 45° C.) and then the temperature was raised. At 100° C. all of the solids had dissolved and heating was continued to 118° C. and was maintained at 115° C. for 4 h. The mixture was poured into water (3750 mL) carefully as gas began to evolve and the temperature of the aqueous solution rose to approximately 45° C. and was allowed to sit at room temperature over two nights. To the resulting mixture was added water (6000 mL) and was extracted with methylene chloride (3×2000 mL), washed with water (3×1000 mL) and the solvent removed in vacuo to give a brownish yellow liquid, with much pyridine present. The vacuum pump was connected to the rotary evaporator to remove the residual pyridine. The residue (brown solid) was triturated with diethyl ether (3×1500 mL), treated with decolorizing carbon and the solvent removed in vacuo to give a solid which contained pyridine. The yellow solid was slurried in water (2×200 mL) and dried in vacuo at 60° C. to give 63.2 g of a light yellow solid (62.8% yield): mp 186–187° C.; TLC [50/50 ethyl acetate/hexanes] showed amide at Rf=0.31 and thioamide Rf=0.53; $^1$H NMR (DMSO-d$_6$) δ10.6 (bs, 1H), 10.0 (bs, 1H), 8.6 (s, 2H).

The following step illustrates the preparation of the S-methyl imidate of formula (12a). Into a 3 L three necked flask equipped with a magnetic stirrer was added acetone (80 mL) and 3,5-dichloro-4-pyridylthioamide (15.87 g, 76.6 mmol). To the stirred solution iodomethane (10.89 g, 4.77 mL, 76.6 mmol) was added dropwise. The slurry was stirred over night. The resulting yellow solids were removed via filtration and washed with ether to obtain 15.23 grams (57%) of S-methylthio-3,5-dichloro-4-pyridylimidinium iodide: mp 158–161° C. $^1$H NMR (DMSO-d6) δ8.8 (s, 2H), 7.8 (bs, 2H), 2.6 (s, 3H).

Preparation 3

N-(3-Methyl-2-thienoyl)-S-methylthio-3,5-dichloro-4-pyridlimidate (13a)

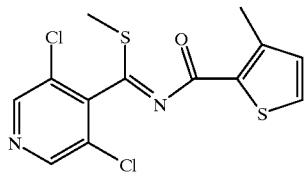

(13a)

Pyridine (0.51 mL, 6.3 mmol) was added dropwise to a slurry of 3-methyl-2-thiophenecarbonyl chloride (0.48g, 3.0 mmol) and S-methylthio-3,5-dichloropyridylimidinium iodide (1.05 g, 3.0 mmol) in 5 mL of 1,2-dichloroethane, under N$_2$, at room temperature. After stirring at room temperature for 60 minutes the reaction mixture was poured into H$_2$0 (25 mL) and extracted with ethyl acetate (3×25 ml). The combined organic extracts were washed with H$_2$O (1×25 mL), saturated sodium chloride (1×25 mL), dried over anhydrous MgSO$_4$, filtered and concentrated in vacuo to give 0.99 g of a yellow oil. This was chromatographed over silica gel (MPLC), eluting with 90% hexane/10% ethyl acetate. Isolation of the major product gave 0.827 g (80% yield) of the title compound as a faint yellow solid: mp 99–101° C. $^1$H NMR (CDCl$_3$) δ8.51 (s, 2H), 7.45 (d, 1H), 6.94 (d, 1H), 2.64 (s, 3H), 2.49 (s, 3H).

Preparation 4

1-Methyl-3-(3,5-dichloro-4-pyridyl)-5-(3-methyl-2-thienyl)[1,2,4]triazole (5a)

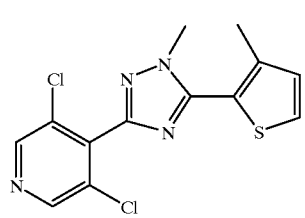

(5a)

Methylhydrazine (0.225 mL, 4.2 mmol) was added dropwise to a solution of the N-acyl-S-methylthioimidate of Example 7 (0.725 g, 2.1 mmol) in 5 mL of toluene, under N$_2$, at room temperature. After stirring at room temperature for 24 hours, TLC analysis showed a 2:1 mixture of starting material to product. An additional 0.2 mL of methylhydrazine was added and the mixture warmed to 40° C. After 5 hours TLC shows a 1:1 mixture of starting material to product. An additional 0.2 mL of methylhydrazine was added and stirring continued for 24 hours at 40–50° C. at which time TLC analysis indicated that all of the starting material had been consumed. The reaction mixture was concentrated in vacuo and the resultant yellow oil was chromatographed over silica gel (MPLC), eluting with 80% hexane/ 20% ethyl acetate. Isolation of the major product gave 0.422 g (65% yield) of the title compound as a faint yellow oil. $^1$H NMR (CDCl$_3$) δ8.61 (s, 2H), 7.47(d, 1H), 7.02(d, 1H), 4.05(s, 3H), 2.40(s, 3H).

Preparation 5

1-n-Butyl-3-(2-chloro-6-fluorophenyl)-5-(3,4,5-trichlorothien-2-yl)-1H[1,2,4] triazole (5b)

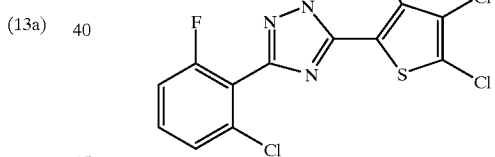

(5b)

A mixture of N-(3 ,4,5-trichloro-2-thienoyl)-S-methylthio-(2-fluoro,6-chloro)-phenylimidate (1.04 g, 2.5 mmol), n-butylhydrazine oxalate (1.78 g, 10 mmol) and triethylamine (4.04 g, 10 mmol) in toluene (20 mL) was heated at 105° C. for 16 h. Upon cooling down, the mixture was diluted with ether—CH$_2$Cl$_2$ (3:1) and washed with 1N HCl, saturated NaHCO$_3$ and brine, dried over anhydrous Na$_2$SO$_4$, purified on silica gel by flash chromatography using ether—CH$_2$Cl$_2$—hexane (15:8:77) as eluting solvent to give 0.48 g of product (5b) as a white solid in 88% yield: mp 110–112° C. $^1$H NMR (CDCl$_3$) δ7.36 (td, J=8.4, 5.4 Hz, 1H), 7.30 (dd, J=7.8, 1.2,1H), 7.10 (td, J=8.4, 1.8 Hz, 1H), 4.24 (t, J=7.2 Hz, 2H), 1.93 (quint, J=7.2 Hz, 2H), 1.31 (hextet, J=7.2 Hz, 2H), 0.91 (t, J =7.2 Hz, 2H). MS (EI): 437 (M$^+$), 402, 367, 226, 197, 156. Anal. Calcd for C$_{16}$H$_{12}$C$_{14}$FN$_3$S: C, 43.76; H, 2.75; N, 9.57. Found: C, 43.80; H, 2.71; N, 9.44.

The final step in the preparation of compounds of formula (1) involve the palladium catalyzed coupling of aryl bromides with terminal acetylene compounds. Therefore, the triazole intermediates of formula (5) were converted to either the aryl bromide or iodide of formula (6) using known procedures. Preparations 6 and 7, hereinafter, illustrate the two step preparation of the aryl bromide of formula (6).
Preparation 6
1-Methyl-3-(2-chloro-6-fluorophenyl)-5-(3,4-dichlorothien-2-yl) [1 2,4]triazole

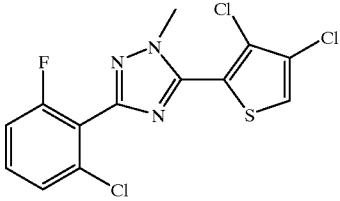

To a solution of 1-methyl-3-(2-chloro-6-fluorophenyl)-5-(3,4,5-trichlorothien-2-yl) (1,2,4)triazole (50.0 g, 126 mmol) in 250 mL of dry THF was added n-BuLi (60.4 mL of 2.5 M, 151 mmol) dropwise at −78° C. The resulting dark solution was stirred at −78° C. for 1 hour. TLC analysis (25%EtOAC/Pentane) indicates residual compound (5b). Added additional n-BuLi (4 mL, 1.6 mmol) and stirred at −78° C. for 1 hour. The reaction was quenched with saturated aqueous ammonium chloride and warmed to room temperature. The phases were separated and the aqueous residue was extracted with methylene chloride (100 mL). The organics were evaporated at reduced pressure, and the resulting dark oil was dissolved in methylene chloride, washed with brine, dried (sodium sulfate), filtered, and the solvent evaporated at reduced pressure to give the crude product as a dark oil. Flash chromatography (Silica Gel, 15%EtOAc/Pentane) affords 33.46 g (73%) of the desired product as a tan solid: mp 118–120° C $^1$H NMR (CDCl$_3$) δ4.03 (s, 3H), 7.08–7.14 (Ar-m, 1H), 7.29–740 (Ar-m, 2H), 7.50 (s, 1H).
Preparation 7
1-Methyl 3-(2-chloro-6-fluorophenyl)-5-(5-bromo-3,4-dichlorothien-2-yl) [1,2,4]triazole (6a)

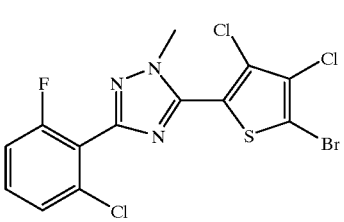

To a mixture of 1-methyl-3-(2-chloro-6-fluorophenyl)-5-(3,4-dichlorothien-2-yl) [1,2,4]triazole (33.4 g, 92.1 mmol) and sodium acetate (7.6 g, 92.1 mmol) in acetic acid (250 mL) was added bromine (58.9 g, 368.4 mmol) dropwise at a rate which maintained the reaction temperature below 35° C. The resulting mixture was slowly heated to 70° C. and stirred for 2.5 hours, cooled to 50° C. and stirred overnight, and cooled to room temperature. TLC analysis (methylene chloride) indicates full consumption of the starting material. The reaction was slowly poured into a mixture of 10% aqueous sodium bisulfite and ice (300 mL), and the resulting pale yellow suspension was stirred for 20 minutes. The solids were collected by vacuum filtration, washed with water, and dissolved in methylene chloride. The organics were dried (sodium sulfate), filtered, and the solvent evaporated at reduced pressure to give 39.3 g (96%) of desired product as a tan solid: mp 178–180° C. $^1$H NMR (CDCl$_3$) δ4.04 (s, 3H), 7.08–7.14 (Ar-m, 1H), 7.29–7.40 (Ar-m, 2H).
As stated above, compounds of formula (1) can be prepared by coupling the triazole intermediate of formula (6) with trimethylsilyl acetylene to give an intermediate of formula (8) (*J Am. Chem Soc.* 1985, 107, 5670 and *J Heterocylic Chem.* 1995, 32, 1261). The trimethylsilyl group can be removed using standard conditions (J Med. Chem. 1987, 30, 1433 and Tetrahedron Lett. 1993, 34, 1223) to give the terminal acetylene intermediate of formula (9). Examples 3 and 4, hereinafter, illustrate the preparation of the trimethylsilyl acetylene intermediate of formula (8) and the terminal acetylene of formula (9).

Example 3 1-Methyl-3-(2-chloro-6-fluorophenyl)-5-(3,4-dichloro-5-(2-trimethylsilyl-ethynyl)-thien-2-yl) [1 2,4]triazole (8a)

(8a)

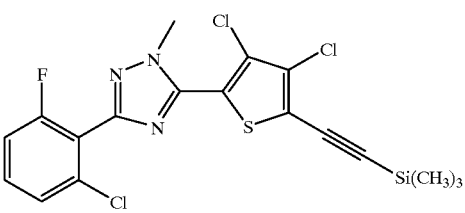

To a mixture of 1-methyl 3-(2-chloro-6-fluorophenyl)-5-(5-bromo-3,4-dichlorothien-2-yl)[1,2,4]triazole (30.0 g, 68.0 mmol), TMS-acetylene (25.0 g, 254.0 mmol), cuprous iodide (0.78 g, 4.1 mmol), and tetrakis(triphenylphosphine) palladium(0) (2.36 g, 2.0 mmol) in toluene (300 mL) was added triethylamine (8.6 g, 85.0 mmol) at room temperature. The mixture was heated to reflux and stirred for 3 hours. TLC analysis (methylene chloride) shows complete consumption of the starting material. The mixture was cooled to room temperature, poured into water, filtered through celite, and extracted with ethyl acetate (3×150 mL). The organics were washed with brine, dried (sodium sulfate), filtered, and the solvent removed under reduced pressure to give the crude product as a dark oil. Flash chromatography (Silica Gel, 10% EtOAc/Pentane) gives the product as a yellow solid. Trituration with hexanes affords 17.0 g (54%) of a white solid: mp 102–104° C. $^1$H NMR (CDCl$_3$) δ0.30 (s, 9H), 4.02 (s, 3H), 7.08–7.25 (Ar-m,1H), 7.29–7.40 (Ar-m, 2H).

EXAMPLE 4
1-Methyl-3-(2-chloro-6-fluorophenyl)-5-(3,4-dichloro-5-ethynvl-thien-2-yl)[1,2,4]triazole (9a)

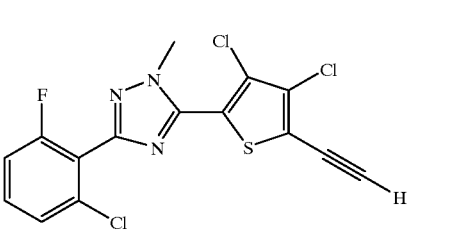

To a mixture of 1-methyl-3-(2-chloro-6-fluorophenyl)-5-(3,4-dichloro-5-(2-trimethylsilyl-ethynyl)-thien-2-yl) [1,2,4] triazole (5.0g, 10.9 mmol) in methanol (20 mL) was added potassium carbonate (1.66 g, 12 mmol) at 0° C., and the resulting off-white suspension was stirred at 0° C. for 3.5 hours. TLC analysis (10% EtOAc/Pentane) indicates complete conversion to product. The reaction was acidified with 2 N hydrochloric acid and extracted with ether (2×100 mL). The organics were combined, washed with brine, dried (sodium sulfate), filtered, and the solvent evaporated under reduced pressure to give a tan solid. Trituration with pentane affords 4.06 g (96%) of product as a tan powder: mp 145–165 (slow decomposition) $^1$H NMR (CDCl$_3$) δ3.77 (s, 1H,), 4.04 (s, 3H), 7.08–7.14 (m, 1H), 7.29–7.40 (Ar-m, 2H).

Compounds of formula (1) can be prepared by coupling the triazole intermediate of formula (9) with aryl halides of formula (10) under palladium catalysis, wherein Ar, R1, Q, and R2 are defined as in formula (1) above. Preparations 8 and 9, hereinafter, illustrate the preparation of the aryl halides of formula (10) from commercially available starting materials. Furthermore, examples 5 and 6, hereinafter, illustrates the synthesis of a compound of formula (1) utilizing the palladium-catalyzed reaction between triazole intermediate of formula (9) with aryl halides of formula (10).

Preparation 8
3-Fluoro-4-iodotoluene (10a)

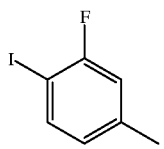

(10a)

To a suspension of 2-fluoro-4-methylaniline (2.0 g, 16 mmol) in aqueous sulfuric acid (~7 N) was added an aqueous solution of sodium nitrite (1.10 g, 16 mmol, 10 mL water) dropwise at 0° C. and the resulting light orange solution was stirred for 30 minutes. This solution was carefully poured into an aqueous solution of potassium iodide (3.98 g, 24 mmol, 16 mL water) at 80° C. and the resulting red mixture was stirred 1.5 hours at 80° C., and overnight at 50° C. The reaction was cooled to room temperature, poured into water (300 mL), and sodium bisulfite added until the light yellow color remained constant. The aqueous was extracted with diethyl ether (2×125 mL) and the organics were combined, washed with brine, dried (sodium sulfate), filtered, and the ether evaporated to give 2.5 g (66%) of crude product as a yellow green oil. Used without further purification. $^1$H NMR (CDCl$_3$) δ2.32 (s, 3H,), 6.72 (dd, 1H, J=1.28 Hz, J=8.05 Hz), 6.88 (dd, 1H, J=1.28 Hz, JH=8.97 Hz), 7.58 (dd, 1H, J=1.08 Hz, J=6.78 Hz).

Preparation 9
2-Iodo-6-methylpyridine (10b)

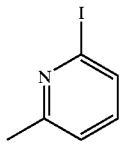

(10b)

To a solution of 2-bromo-6-methylpyridine (2.0 g, 11.6 mmol) and sodium iodide (2.78 g, 18.6 mmol) in dry acetonitrile (13 mL) was added acetyl chloride (1.9 g, 24.4 mmol) dropwise, and the resulting light yellow suspension was heated to reflux. G.C. analysis after 16 hours at reflux indicated only 50% conversion. Added additional acetyl chloride (1 equivalent) and sodium iodide (0.8 equivalent) and refluxed for 16 hours. G.C. analysis indicated 90% conversion to desired product in addition to the expected bromo and chloro by-products. The reaction was cooled to room temperature, diluted with aqueous potassium carbonate and sodium bisulfite (75 mL, 10 and 5% respectively), and extracted with diethyl ether (2×75 mL). The organics were combined, washed with the carbonate/bisulfite solution, dried (sodium sulfate), filtered, and the solvent evaporated under reduced pressure to give 2.39 g (94%) of crude product as a dark oil. Used without further purification. $^1$H NMR (CDCl$_3$) δ2.52 (s, 3H,), 7.10 (d, 1H, J=7.51 Hz), 7.20 (t, 1H, J=7.69 Hz, J=7.51 Hz), 7.58 (d, 1H, J=7.69 Hz). (Tetrahedron Lett. 1990, 31, 6757)

EXAMPLE 5
3-(2-chloro-6-fluorophenyl)-5-(5-(2,4-difluorophenylalkynyl)-3,4-dichloro-2-thiophene)-1-methyl-1H-1,2,4-triazole (1b)

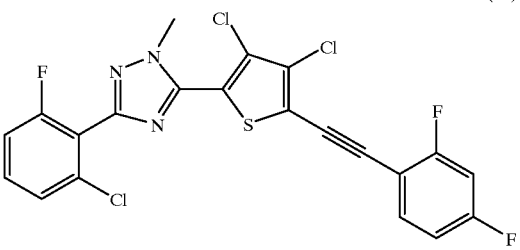

(1b)

2,4-Difluoroiodobenzene ((0.62g, 2.6 mmol), 3-(2-chloro-6-fluorophenyl)-5-(5-alkynyl-3,4-dichloro-2-thiophene)-1-methyl-1H-1,2,4-triazole (1.0g, 2.6 mmol) and copper(I) iodide (49mg, 0.26 mmol) was added to dry dimethylformamide (8 mL) and triethylamine (8 mL) and stirred at room temperature for 5 minutes. Bis-triphenylphosphinepalladium(II) chloride (180 mg, 0.26 mmol) was then added to the solution. This was stirred at 70° C. for 60 minutes, cooled to room temperature and poured into dilute hydrochloric acid (1M, 150 mL) and extracted with diethyl ether (3×40 mL). Combined organic layers were washed with water (2×70 mL) and brine (50 mL) before drying over magnesium sulphate. After concentration under reduced pressure, the residue was applied to a dry flash silica column and eluted with acetonitrile : methylene chloride : hexane(1:4:10). The second fraction was collected and recrystallised from hexane to give orange prisms. Yield 0.77g (60%). Mp 149° C. $^1$H (CDCl$_3$) δ7.6 (m, 1H), 7.2–7.4 (m, 2H), 7.1(t, 1H), 6.9 (m, 2H), 4.0 (s,3H).

EXAMPLE 6
1-Methyl-3-(2-chloro-6-fluorophenyl)-5-(3,4-dichloro-5-(2-(2-diethylaminopvrimidin-4-yl)ethynynl)-thien-2-yl)[1,2,4]triazole (1c)

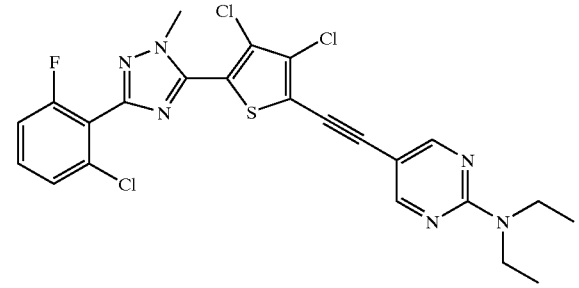

(1c)

To a mixture of 1-methyl-3-(2-chloro-6-fluorophenyl)-5-(3,4-dichloro-5-ethynyl-thien-2-yl)[1,2,4]triazole (0.50 g, 1.3 mmol), 2-chloro-4-iodopyrimidine (0.313 g, 1.3 mmol), and cuprous iodide (0.0025 g, 0.13 mmol) in triethylamine and N,N-dimethylformamide (1:1, 6 mL total volume) was added bistriphenylphosphine palladium(II)chloride and the resulting black mixture was heated to 60° C. and stirred for 2 hours. TLC analysis (10% EtOAc/hexane) shows complete consumption of the starting material. The reaction was cooled to room temperature, diluted with diethyl ether and washed with brine, dried (magnesium sulfate), filtered, and the solvent evaporated. Chromatography (SiO$_2$, 10% EtOAc-Hex) afforded the product as a yellow solid. (188 mg, 28%) Mp 152–154° C. $^1$H NMR δ8.46 (s, 2H), 7.29–7.38 (m, 2H), 7.08–7.14 (m, 1H) 4.05 (s, 3H) 3.66 (q, 4H) 1.21 (t, 6H).

Compounds of formula (1) can also be prepared by coupling the triazole intermediate of formula (6) with terminal alkynes of formula (7) under palladium catalysis, wherein Ar, R1, Q, and R2 are defined as in formula (1) above. Examples 7 and 8, hereinafter, illustrates the synthesis of a compound of formula (1) utilizing the palladium catalyzed reaction between triazole intermediate of formula (6) with terminal alkynes of formula (7). The terminal alkyne of formula (7) is commercially available or readily synthesized using standard methods.

EXAMPLE 7

1-Methyl-3-(2-Chloro-6-fluorophenyl)-5-(3,4-dichloro-5-(2-(4-n-hexyl)phenyl)-ethynyl-thien-2-yl)-1H[1,2,4]triazole (1d)

(1d)

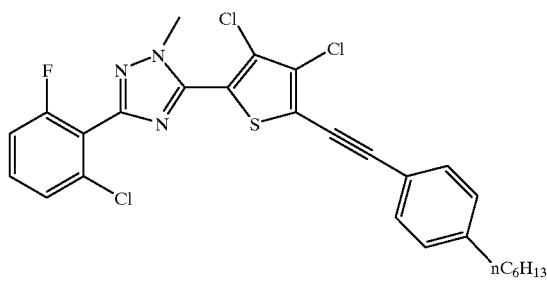

To a heating-gun dried 50 mL three-neck flask equipped with a magnetic stirrer and electronic thermometer was charged with 3-(2-fluoro-6-chlorophenyl)-5-(3,4-dichloro-5-bromothien-2-yl)-1-methyl[1,2,4]triazole (0.441 g, 1.0 mmol), 4-n-hexylphenylacetylene (0.279 g, 1.5 mmol), dichloro-bis(triphenylphosphine)palladium(II) (0.070 g, 0.1 mmol), cuprous iodide (0.019 g, 0.1 mmol), DMF (2.5 mL), and triethylamine (2.5 mL) under nitrogen. The reaction mixture was heated at 51° C. for 2 h and poured into 1N HCl aqueous solution under stirring upon cooling down. The mixture was then extracted with ether (3×35 mL) and the combined organic layer was washed with saturated NaHCO$_3$ solution, water (2×30 mL), brine (30 mL), and dried over anhydrous MgSO$_4$. After filtration followed by removal of the solvent, the residue was purified on silica gel by flash chromatography using 80:19:1 hexane—CH$_2$Cl$_2$—CH$_3$CN as eluting solvent to provide 0.31 g of product as a brownish oil in 57% yield: $^1$H NMR (CDCl$_3$) δ7.36 (d, J=8.1 Hz, 2 H), 7.13–7.26 (m, 2H), 7.06 (d, J=8.1 Hz, 2H), 6.97 (td, J=9.0, 1.5 Hz, 1H), 3.91 (s, 3H), 2.50 (t, J=7.5 Hz, 2H), 1.47 (m, 2H), 1.12–1.24 (m, 6H), 0.76 (t, J=6.6 Hz, 3H).

EXAMPLE 8

1-Methyl-3-(2-Chloro-6-fluorophenyl)-5-(2,3-dichloro-4-(2-(4-trifluoromethyl)phenyl)-ethynyl-phenyl)-1 H[1,2,4]triazole (1 e)

(1e)

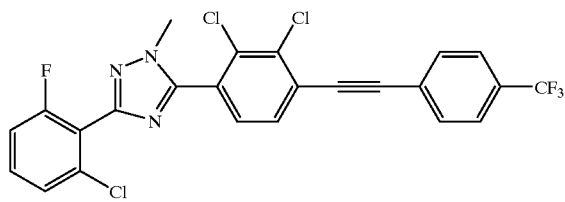

A dry 50 mL three-neck flask cooled in an ice-water bath was charged with 3-(2-chloro-6-fluorophenyl)-5-(2,3-dichloro-4-iodophenyl)-1-methyl[1,2,4]triazole (0.241 g, 0.5 mmol), 4-trifluoromethyl phenylacetylene (0.128 g, 0.75 mmol), dichlorobis(triphenylphosphine)palladium(II) (0.035 g, 0.05 mmol), cuprous iodide (0.0095 g, 0.05 mmol), DMF (1.7 mL), and triethylamine (1.7 mL) under nitrogen atmosphere. The reaction mixture was continued to stir at 0° C. until the reaction completed monitored by TLC (1h). The mixture was poured into aqueous acidic solution (1N HCl or H$_2$SO$_4$), and extracted with ether—CH$_2$Cl$_2$ (4:1). The organic layer was washed with water, saturated NaHCO$_3$ solution and brine successively, and dried over anhydrous MgSO$_4$. After filtration followed by removal of the solvent, the residue was purified on silica gel by flash chromatography using 4:1:15 ether—CH$_2$Cl$_2$—hexane as eluent to provide 0.239 g of product as a white solid in 92% yield: mp 138–140° C. $^1$H NMR (CDCl$_3$) δ7.72 (d, J=8.4 Hz, 2H), 7.66 (d, J=8.4 Hz, 2H), 7.64 (d, J=8.0 Hz, 1H), 7.50 (d, J=8.0 Hz, 1H), 7.30–7.40 (m, 2H), 7.12 (m, 1H), 3.91 (s, 3H).

The compounds identified in the following Tables 1–7 were prepared using the procedures illustrated in the foregoing examples, and the compounds were tested against tobacco budworm, beet armyworm, cabbage looper, cotton aphid, two-spotted spider mite, sweetpotato whitefly, brown planthopper, and green leafhopper using procedures described hereinafter.

TABLE 1

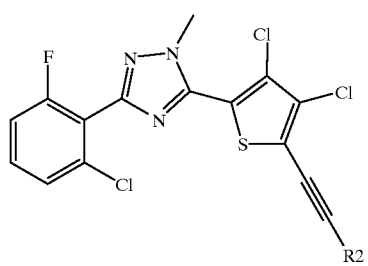

| Compound # | R2 | mp | TBW | BAW | CL | CA | SM | WF | BPH | GLH |
|---|---|---|---|---|---|---|---|---|---|---|
| 1 | —Si(CH$_3$)$_3$ | 102–104 | A | A | A | E | B | F | F | B |
| 2 | —H | 145–165 | G | G | F | D | G | G | D | F |

TABLE 1-continued
| Compound # | R2 | mp | TBW | BAW | CL | CA | SM | WF | BPH | GLH |
|---|---|---|---|---|---|---|---|---|---|---|
| 3 | —C(CH$_3$)$_3$ | oil | D | G | A | A | B | F | | |
| 4 | —Ph | 133–135 | F | A | A | B | D | F | E | G |
| 5 | —CH$_2$CH$_3$ | oil | G | G | G | B | G | F | F | F |
| 6 |  —OEt | 160–162 | G | A | A | A | G | G | F | F |
| 7 |  —OMe | 140–142 | F | A | A | D | | | | |
| 8 | 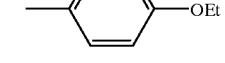 —Cl | 155–157 | F | A | A | F | A | G | F | F |
| 9 | 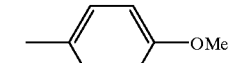 F | 135 | A | B | A | | | F | F | |
| 10 | 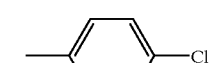 —CH$_3$ | 153–154 | G | A | D | B | F | G | E | G |
| 11 |  Cl | 118–119 | A | B | A | D | G | G | G | E |
| 12 | 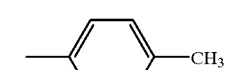 —F | 156–157 | G | A | A | C | G | F | F | F |
| 13 |  —CH$_2$CH$_3$ | 101–102 | G | A | A | C | G | F | G | G |
| 14 | 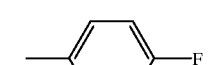 —nPr | 104–105 | A | A | A | A | G | F | F | G |
| 15 | 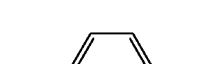 —OnPr | 153–154 | F | D | D | D | G | F | F | F |

TABLE 1-continued
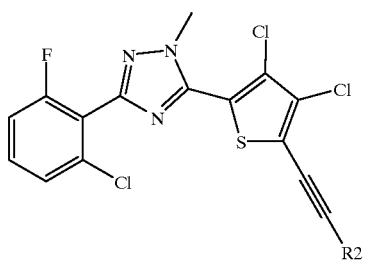
| Compound # | R2 | mp | TBW | BAW | CL | CA | SM | WF | BPH | GLH |
|---|---|---|---|---|---|---|---|---|---|---|
| 16 | 4-phenylphenyl | 155–157 | G | F | D | F | G | F | F | F |
| 17 | 4-hydroxyphenyl | 205–207 | G | G | G | F |  | F | D | F |
| 18 | 3-fluoro-4-methylphenyl | 160–161 | B | A | A | F | A | G | E | F |
| 19 | 3-methyl-4-fluorophenyl | 123–125 | B | A | A | G | E | G | D | F |
| 20 | 3-methyl-4-fluorophenyl | 105–107 | A | A | A | D | B | F | F | G |
| 21 | 4-methylpyridin-3-yl | 127–129 | G | G | G | F | G | G | F | G |
| 22 | 2,6-dichloro-4-(OCH$_2$CF$_3$)phenyl | 165–166 | G | G | G | F | G | D | F | F |
| 23 | 3,4-difluorophenyl | 149 | G | A | A | F | G | F | G | F |
| 24 | 4-(CF$_3$)phenyl | 140–142 | G | A | A | D | G | F | F | F |

TABLE 1-continued
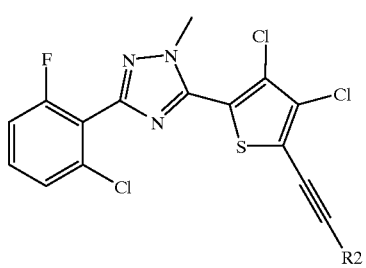
| Compound # | R2 | mp | TBW | BAW | CL | CA | SM | WF | BPH | GLH |
|---|---|---|---|---|---|---|---|---|---|---|
| 25 |  | 75–77 | A | A | A | D | G | E | D | F |
| 26 |  | 161 | A | G | A | F | G | D | C | F |
| 27 |  | 150 | D | A | A | G | F | D | E | F |
| 28 |  | 133–134 | A | A | A | F | G | D | F | D |
| 29 |  | 154–156 | A | G | A | E | G | F | F | F |
| 30 |  | 128–131 | G | A | G | F | G | E | B | F |
| 31 | 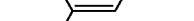 | 123–125 | G | A | A | D | G | F | F | F |
| 32 |  | 165–167 | G | G | G | F | G | C | D | F |

TABLE 1-continued
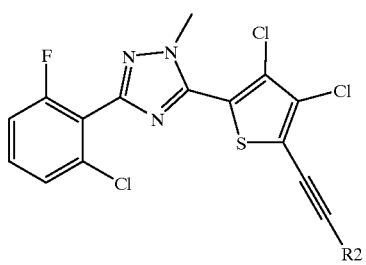
| Compound # | R2 | mp | TBW | BAW | CL | CA | SM | WF | BPH | GLH |
|---|---|---|---|---|---|---|---|---|---|---|
| 33 | 2-pyridyl | 148–150 | G | G | G | F | G | D | F | F |
| 34 | 3-pyridyl | 112–114 | G | G | A | E | G | D | D | F |
| 35 | 2-thienyl | 131–135 | G | G | A | E | G | F | F | G |
| 36 | 3-methyl-2-thienyl | 144–145 | G | G | A | E | G | F | D | D |
| 37 | 2,5-difluorophenyl | 141 | F | D | A | D | B | E | F | F |
| 38 | isobutenyl | oil | G | G | G | D | G | F | | |
| 39 | propenyl | oil | G | G | G | B | G | G | F | F |
| 40 | 2,6-dimethylphenyl | 119–122 | G | B | G | B | G | G | | |
| 41 | 2-(diethylamino)pyrimidin-5-yl | 152–154 | D | A | B | F | F | F | E | G |

TABLE 1-continued
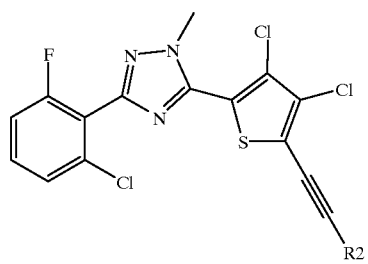
| Compound # | R2 | mp | TBW | BAW | CL | CA | SM | WF | BPH | GLH |
|---|---|---|---|---|---|---|---|---|---|---|
| 42 | 2,5-dimethylthiophene | 129–132 | B | D | A | C | G | F | F | F |
| 43 | 2,4-dimethylpyridine | 183–184 | G | G | G | F | G | F | G | F |
| 44 | 2,6-dimethylpyridine | 133–135 | G | G | G | F | G | F | G | G |
| 45 | 2,3-dimethylpyridine | 182–183 | G | G | G | F | G | F | F | F |
| 46 | 3-thienyl | 120–124 | G | D | D | E | G | F | F | G |
| 47 | 2-CF3, 4-F-phenyl | 103–105 | A | A | A | C | G | G | F | G |
| 48 | 2-Cl, 4-OMe-phenyl | 165–167 | G | A | A | D | G | G | F | G |
| 49 | 2-CF3, 4-OCH2CH3-phenyl | 118–120 | D | A | A | F | G | F | F | G |
| 50 | 5-Cl-2-methylthiophene | 130–133 | G | G | A | D | G | F | D | F |

TABLE 1-continued

| Compound # | R2 | mp | TBW | BAW | CL | CA | SM | WF | BPH | GLH |
|---|---|---|---|---|---|---|---|---|---|---|
| 51 | 2-F,4-CH₃-phenyl | 155–158 | B | A | A | F | G | F | F | F |
| 52 | 2-CH₃,4-F-phenyl | 123–125 | A | A | A | D | G | F | G | G |
| 53 | 3-CH₃-phenyl | 107–108 | F | A | A | E | G | F | F | G |
| 54 | 4-nC₆H₁₃-phenyl | oil | A | A | B | E | G | F | F | F |
| 55 | 4-nC₇H₁₅-phenyl | oil | D | A | A | F | G | F | F | F |
| 56 | 4-OC₇H₁₅-phenyl | 84–86 | A | A | A | E | G | F | F | G |
| 57 | 2-CH₃-pyridin-4-yl | 143–144 | G | G | G | G | G | F | G | F |
| 58 | 2-methyl-5-methyl-pyridinyl | 166–168 | G | G | G | F | G | F | F | F |
| 59 | 2-CF₃O,4-Br-phenyl | 83–85 | G | G | G | F | G | F | F | F |

TABLE 1-continued
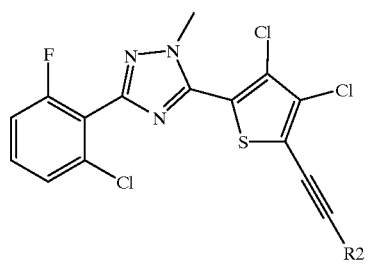
| Compound # | R2 | mp | TBW | BAW | CL | CA | SM | WF | BPH | GLH |
|---|---|---|---|---|---|---|---|---|---|---|
| 60 | (2-fluoro-4-methyl-phenyl with OCH₂CH₃) | 137–138 | G | A | A | F | G | E | G | G |
| 61 | (6-methyl-3-chloro-pyridyl) | 189–191 | G | G | G | F | G | F | F | F |
| 62 | (6-methyl-5-CF₃-pyridyl) | 153–155 | G | G | G | F | G | F | F | F |
| 63 | (5-methyl-2-morpholino-pyrimidine) | 158–161 | G | D | A | G | G | F | | |
| 64 | (5-methyl-2-piperidino-pyrimidine) | 155–159 | G | B | A | G | G | F | | |
| 65 | (4-OCF₃-phenyl) | 96–98 | A | A | A | F | | | | |
TABLE 2
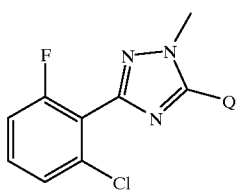
| compound | Q | mp | TBW | BAW | CL | CA | SM | WF | BPH | GLH |
|---|---|---|---|---|---|---|---|---|---|---|
| 66 |  | 120–122 | G | GG | G | B | G | F | G | F |

TABLE 2-continued
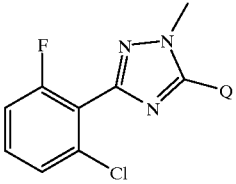
| compound | Q | mp | TBW | BAW | CL | CA | SM | WF | BPH | GLH |
|---|---|---|---|---|---|---|---|---|---|---|
| 67 | 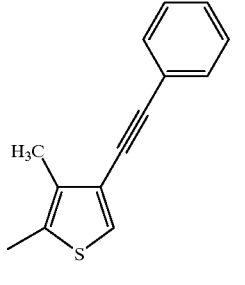 | glass | B | A | G | A | B | F | G | G |
| 68 | 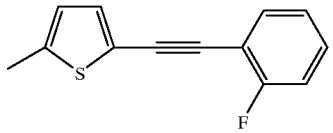 | 114–116 | G | G | G | A | G | F | F | F |
| 69 | 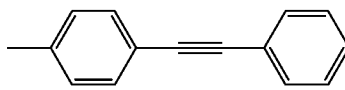 | 155–157 | G | G | G | E |  | F | G | F |
| 70 | 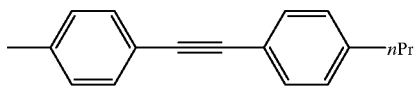 | 116–117 | G | G | G | C |  | F | G | G |
| 71 | 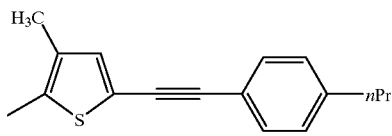 | 133–134 | G | G | G | A |  | F | F | G |
| 72 |  | 105–106 | G | A | B | C | F | F | F | G |

TABLE 3

[Structure: 1-methyl-3-Ar-1,2,4-triazole linked to 3,4-dichlorothiophene with alkynyl-(4-n-propylphenyl) group]

| compound number | Ar | mp | TBW | BAW | CL | CA | SM | WF | BPH | GLH |
|---|---|---|---|---|---|---|---|---|---|---|
| 73 | 2,6-difluorophenyl | 92 | A | A | F | F | G | F | A | G |
| 74 | phenyl | 147 | F | F | G | F | G | F | F | F |
| 75 | CH₃— | 75–77 | G | G | G | F | G | F | C | F |
| 76 | 2-fluorophenyl | 125 | G | A | G |   | G | F | F | F |

TABLE 4

[Structure: 1-methyl-3-Ar-1,2,4-triazole linked to 3,4-dichlorothiophene with alkynyl-(4-fluorophenyl) group]

| compound | Ar | mp | TBW | BAW | CL | CA | SM | WF | BPH | GLH |
|---|---|---|---|---|---|---|---|---|---|---|
| 77 | 2,6-difluorophenyl | 149 | G | A | A | F | D | D | F | F |

TABLE 4-continued
| compound | Ar | mp | TBW | BAW | CL | CA | SM | WF | BPH | GLH |
|---|---|---|---|---|---|---|---|---|---|---|
| 78 | $CH_3-$ | 133–135 | G | A | G | F | G | D | F | F |
| 79 | (2-F-phenyl) | 179 | G | G | G | F | G | D | F | F |
TABLE 5
| compound | R1 | mp | TBW | BAW | CL | CA | SM | WF | BPH | GLH |
|---|---|---|---|---|---|---|---|---|---|---|
| 80 | H | 209–211 | G | G | G | G | G | F | | |
| 81 | $-CH_2CH_3$ | oil | F | A | D | F | G | F | | |
| 82 | $-nC_4H_9$ | oil | G | D | A | F | G | F | | |
| 83 | (cyclohexyl) | 135–137 | G | G | G | F | G | F | | |
| 84 | (4-Cl-phenyl) | 125–126 | G | G | G | F | G | F | | |

TABLE 6
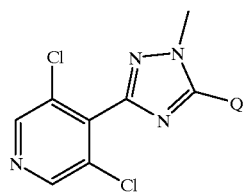
| compound | Q | mp | TBW | BAW | CL | CA | SM | WF | BPH | GLH |
|---|---|---|---|---|---|---|---|---|---|---|
| 85 | 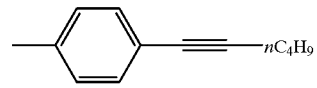 | oil | G | G | G | B | G | F | E | F |
| 86 | 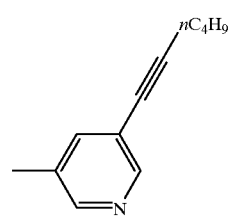 | 77–80 | G | G | G | E | C | F | F | F |
| 87 | 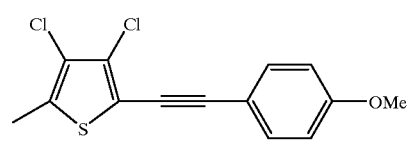 | oil | F | F | F | | | | | |
| 88 | 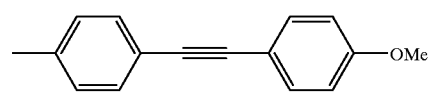 | 162–164 | G | G | G | D | G | F | G | F |
| 89 | 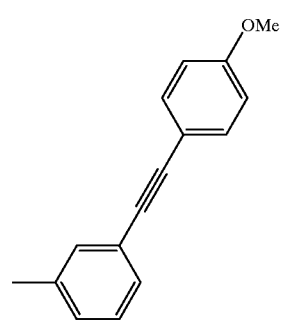 | oil | G | G | G | B | G | F | G | F |

TABLE 7

[Structure: 3-(2-fluoro-6-chlorophenyl)-1-methyl-5-(2,3-dichloro-4-(C≡C-R2)phenyl)-1H-1,2,4-triazole]

| compound | R2 | mp | TBW | BAW | CL | CA | SM | WF | BPH | GLH |
|---|---|---|---|---|---|---|---|---|---|---|
| 90 | —C₆H₄—nC₃H₇ | oil | G | A | A | B | G | F | E | F |
| 91 | —C₆H₄—OCH₂CH₃ | 147–148 | G | A | B | A | G | F | F | F |
| 92 | —C₆H₄—F | 123–125 | G | A | A | A | F | F | F | F |
| 93 | —C₆H₄—OMe | oil | G | A | A | E | G | F | F | F |
| 94 | —C₆H₄—CF₃ | 138–140 | D | A | A | B | G | F | | |
| 95 | —C₆H₃(F)(CH₃) | 148–150 | F | B | B | C | G | F | | |
| 96 | —Si(CH₃)₃ | 121–123 | F | A | A | D | D | F | | |
| 97 | —H | 125–127 | G | G | G | B | G | F | | |
| 98 | —C₆H₄—OCF₃ | oil | A | A | A | C | | | | |

TBW refers to activity at 400 ppm against tobacco budworm,
BAW refers to activity at 400 ppm against beet armyworm,
CL refers to activity at 400 ppm against cabbage looper,
CA refers to activity at 50 ppm against cotton aphid,
SM refers to activity at 2.5 ppm against two-spotted spider mite,
WF refers to activity at 200 ppm against whitefly,
BPH refers to activity at 10 ppm against brown planthopper, and
GLH refers to activity at 10 ppm against green leafhopper.
In each case the rating scale is as follows

| % Control | Rating |
|---|---|
| 90–100 | A |
| 80–89 | B |
| 70–79 | C |
| 60–69 | D |
| 50–59 | E |
| less than 50 | F |
| inactive | G |

Insecticide and Miticide Utility

The compounds of the invention are useful for the control of insects, mites, and aphids. Therefore, the present invention also is directed to a method for inhibiting an insect, mite, or aphid which comprises applying to a locus of the insect or mite an insect- or mite-inhibiting amount of a compound of formula (1).

The compounds are useful for reducing populations of insects and mites and are useful in a method of inhibiting an insect or mite population which comprises applying to a locus of the insect or mite an effective insect- or mite-inactivating amount of a compound of formula (1). The "locus" of insects or mites is a term used herein to refer to the environment in which the insects or mites live or where their eggs are present, including the air surrounding them, the food they eat, or objects which they contact. For example, plant-ingesting insects or mites can be controlled by applying the active compound to plant parts that the insects or mites eat, particularly the foliage. It is contemplated that the compounds might also be useful to protect textiles, paper, stored grain, or seeds by applying an active compound to such substance. The term "inhibiting an insect or mite" refers to a decrease in the numbers of living insects or mites, or a decrease in the number of viable insect or mite eggs. The extent of reduction accomplished by a compound depends, of course, upon the application rate of the compound, the particular compound used, and the target insect or mite species. At least an inactivating amount should be used. The terms "insect-inactivating amount" and "mite-inactivating amount" are used to describe the amount, which is sufficient to cause a measurable reduction in the treated insect or mite population. Generally an amount in the range from about 1 to about 1000 ppm active compound is used.

In a preferred embodiment, the present invention is directed to a method for inhibiting a mite or aphid which comprises applying to a plant an effective mite- or aphid-inactivating amount of a compound of formula (1).

Insecticidal test for tobacco budworm (*Heliothis virescens*), beet armyworm (*Spodoptera exigua*), and cabbage looper (*Trichoplusia ni*).

To prepare test solution, the test compound was formulated at 400 ppm in 7.5 mL of 2 acetone: 1 tap water. 250 µl of the test solution was pipetted upon the surface of 8 mL of lepidopteran diet (modified Shorey) contained in each of five one-ounce plastic cups (one cup=1 replication). A second-instar beet armyworm was placed upon the treated diet in each cup once the solvent had air-dried. The solutions remaining after completing applications to the one-ounce cups were then used as leaf-dip solutions for 3.5 cm leaf discs cut from cabbage leaves and cotton cotyledons. Five discs of each type of plant were dipped until thoroughly coated into each rate of each compound (=5 replications of each treatment). After air-drying, the treated leaf discs were placed individually into one-ounce plastic cups. Each dried, treated cotton cotyledon disc was infested with a $2^{nd}$ instar tobacco budworm larva, and each cabbage leaf disc was infested with a $2^{nd}$ instar cabbage looper larva. Cups containing the treated substrates and larvae were capped and then held in a growth chamber at 25° C., 50–55% R.H., and 14 hr light: 10 hr dark for 5 days. The number of dead insects of 5 per species per treatment was then determined and the results are given in Table 1–7.

Insecticidal test for cotton aphid (*Aphis gossypii*)

To prepare spray solutions, 1 mg of each test compound was dissolved into 2 nL of a 90:10 acetone:ethanol solvent. This 1 mL of chemical solution was added to 19 mL of water containing 0.05% Tween 20 surfactant to produce a 50 ppm spray solution.

Squash cotyledons were infested with cotton aphid (all life stages)16–20 hours prior to application of spray solution. The solution was sprayed on both sides of each infested squash cotyledon (0.5 mL X 2 each side) with a sweeping action until runoff. The plants were allowed to air dry and held for 3 days in a controlled room at 26° C. and 40% RH after which time the test was graded. Grading was by actual count using a dissecting microscope and comparison of test counts to the untreated check. Results are given in Table 1–7 as percent control based on population reduction versus the untreated.

Insecticidal test for two-spotted spider mite (*Tetranychus urticae*)

Ovicide Method:

Ten adult female two-spotted spider mites were placed on eight 2.2 cm leaf discs of cotton leaf, allowed to oviposit over 24 hours, and thereafter removed. The leaf discs were sprayed with 100 ppm test solutions using a hand syringe, then allowed to dry with sixteen discs left untreated as a negative control. Discs were placed on an agar substrate and held at 24° C. and 90% relative humidity for 6 days. Percent control based on the number of hatched larvae on treated discs and the number on untreated discs is reported in Table 1–7.

Insecticidal test for Sweetpotato Whitefly (*Bemisia tabacia*)

Four mg of each test compound were dissolved by adding 4 mL of a 90:10 acetone:ethanol solvent mixture to the vial containing the sample compound. This solution was added to 16 mL of water containing 0.05% Tween 20 surfactant to produce 20 ml of an 200 ppm spray solution.

Five-week-old cotton plants reared in a greenhouse were stripped of all foliage except for the two uppermost true leaves that were greater than 5 cm in diameter. These plants were then placed into a laboratory colony of whiteflies for two days for oviposition by the colony females. All whiteflies were then removed from the test plants with pressurized air. The spray solution was then applied to the test plants with a hand-held syringe fitted with hollow cone nozzle. One mL of spray solution was applied to each leaf top and bottom for a total of 4 mL per plant. Four replications of each test compound utilized a total of 16 mL spray solution. Plants were air dried and then placed in a holding chamber (28° C. and 60% RH) for 13 days. Compound efficacy was evaluated by counting, under an illuminated magnifying glass, the number of large nymphs (3rd–4th instar) per leaf. Percent control based on reduction of large nymphs of a test compound compared to solution-only (no test compound) sprayed plants is reported in Table 1–7.

Insecticidal test for Brown Planthopper (*Nilaparvata lugens*) and Green Leafhopper (*Nephotettix cincticeps*)

Ten mg of test substance were dissolved in 1 mL of acetone, making a 10,000 ppm solution. Out of this 10,000 ppm solution, 0.1 ml (100 microlitre) are added to 99.9 ml of water to produce 100 ml of a 10 ppm test solution. Twenty-five ml of 10 ppm test solution were added to each of four glass cylinder cages. Within each cylinder, roots of three to five four-week old rice seedlings are submerged in the test. Five laboratory-reared $3^{rd}$ instar nymphs of either brown planthopper or green leafhopper were introduced into the glass cylinder cages. The cylinders (four replicates per treatment) were held in a growth chamber at 28° C. and 75% relative humidity, with a photoperiod of 14 hours. Mortality is observed 6 days after infestation of insects into the test arena. Results are given in Table 1–7 as percent mortality.

In addition to being effective against mites, aphids, and insects when applied to foliage, compounds of formula (1) have systemic activity. Accordingly, another aspect of the invention is a method of protecting a plant from insects which comprises treating plant seed prior to planting it, treating soil where plant seed is to be planted, or treating soil at the roots of a plant after it is planted, with an effective amount of a compound of formula (1).

Compositions

The compounds of this invention are applied in the form of compositions which are important embodiments of the invention, and which comprise a compound of this invention and a phytologically-acceptable inert carrier. The compositions are either concentrated formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspandable or emulsifiable formulations are either solids, usually known as wettable powders, or liquids usually known as emulsifiable concentrates or aqueous suspensions. Wettable powders, which may be compacted to form water dispersible granules, comprise an intimate mixture of the active compound, an inert carrier, and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional nonionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent and applying it to a granular carrier which has been pre-formed to the appropriate particle size, in the range of from about 0.5 to 3 mm. Such compositions may also be formulated by making a dough or paste of the carrier and compound and crushing and drying to obtain the desired granular particle size.

Dusts containing the compounds are prepared simply by intimately mixing the compound in powdered form with a suitable dusty agricultural carrier, such as kaolin clay, ground volcanic rock, and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Insecticides and acaricides are generally applied in the form of a dispersion of the active ingredient in a liquid carrier. It is conventional to refer to application rates in terms of the concentration of active ingredient in the carrier. The most widely used carrier is water.

The compounds of the invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects, mites, and aphids is not critical and can readily be determined by those skilled in the art in view of the examples above. In general, concentrations of from-10 ppm to 5000 ppm of compound are expected to provide good control. With many of the compounds, concentrations of from 100 to 1500 ppm will suffice. For field crops, such as soybeans and cotton, a suitable application rate for the compounds is about 0.5 to 1.5 lb/A, typically applied in 5–20 gal/A of spray formulation containing 1200 to 3600 ppm of compound. For citrus crops, a suitable application rate is from about 100 to 1500 gal/A spray formulation, which is a rate of 100 to 1000 ppm.

The locus to which a compound is applied can be any locus inhabited by an insect or arachnid, for example, vegetable crops, fruit and nut trees, grape vines, and ornamental plants. Inasmuch as many mite species are specific to a particular host, the foregoing list of mite species provides exemplification of the wide range of settings in which the present compounds can be used.

Because of the unique ability of mite eggs to resist toxicant action, repeated applications may be desirable to control newly emerged larvae, as is true of other known acaricides.

The following formulations of compounds of the invention are typical of compositions useful in the practice of the present invention.

A. 0.75 Emulsifiable Concentrate

| | |
|---|---|
| Compound of formula (1) | 9.38% |
| "TOXIMUL D"(nonionic/anionic surfactant blend) | 2.50% |
| "TOXIMUL H'(nonionic/anionic surfactant blend) | 2.50% |
| "EXXON 200"(naphthalenic solvent) | 85.62% |

B. 1.5 Emulsifiable Concentrate

| | |
|---|---|
| Compound of formula (1) | 18.50% |
| "TOXIMUL D" | 2.50% |

-continued

| | |
|---|---|
| "TOXIMUL H" | 2.50% |
| "EXXON 200" | 76.50% |
| C. 1.0 Emulsifiable Concentrate | |
| Compound of formula (1) | 12.5% |
| N-methylpyrrolidone | 25.00% |
| "TOXIMUL D" | 2.50% |
| "TOXIMUL H" | 2.50% |
| "EXXON 200" | 57.50% |
| D. 1.0 Aqueous Suspension | |
| Compound of formula (1) | 12.00% |
| "PLURONIC P-103"(block copolymer of propylene oxide and ethylene oxide, surfactant) | 1.50% |
| "PROXEL GXL"(biocide/preservative) | .05% |
| "AF-100"(silicon based antifoam agent) | .20% |
| "REAX 88B"(lignosulfonate dispersing agent) | 1.00% |
| propylene glycol | 10.00% |
| veegum | .75% |
| xanthan | .25% |
| water | 74.25% |
| E. 1.0 Aqueous Suspension | |
| Compound of formula (1) | 12.50% |
| "MAKON 10"(10 moles ethyleneoxide nonylphenol surfactant | 1.00% |
| "ZEOSYL 200"(silica) | 1.00% |
| "AF-100" | 0.20% |
| "AGRIWET FR"(surfactant) | 3.00% |
| 2% xanthan hydrate | 10.00% |
| water | 72.30% |
| F. 1.0 Aqueous Suspension | |
| Compound of formula (1) | 12.50% |
| "MAKON 10" | 1.50% |
| "ZEOSYL 200"(silica) | 1.00% |
| "AF-100" | 0.20% |
| "POLYFON H"(lignosulfonate dispersing agent) | 0.20% |
| 2% xanthan hydrate | 10.00% |
| water | 74.60% |
| G. Wettable Powder | |
| Compound of formula (1) | 25.80% |
| "POLYFON H" | 3.50% |
| "SELLOGEN HR" | 5.00% |
| "STEPANOL ME DRY" | 1.00% |
| gum arabic | 0.50% |
| "HISIL 233" | 2.50% |
| Barden clay | 61.70% |
| H. 1.0 Aqueous Suspension | |
| Compound of formula (1) | 12.40% |
| "TERGITOL 158-7" | 5.00% |
| "ZEOSYL 200" | 1.0% |
| "AF-1G0" | 0.20% |
| "POLYFON H" | 0.50% |
| 2% xanthan solution | 10.00% |
| tap water | 70.90% |
| I. 1.0 Emulsifiable Concentrate | |
| Compound of formula (1) | 12.40% |
| "TOXIMUL D" | 2.50% |
| "TOXIMUL H" | 2.50% |
| "EXXON 200" | 82.60% |
| J. Wettable Powder | |
| Compound of formula (1) | 25.80% |
| "SELLOGEN HR" | 5.00% |
| "POLYFON H" | 4.00% |
| "STEPANOL ME DRY" | 2.00% |
| "HISIL 233" | 3.00% |
| Barden clay | 60.20% |
| K. 0.5 Emulsifiable Concentrate | |
| Compound of formula (1) | 6.19% |
| "TOXIMUL H" | 3.60% |
| "TOXIMIUL D" | 0.40% |
| "EXXON 200" | 89.81% |

-continued

| | |
|---|---|
| L. Emulsifiable Concentrate | |
| Compound of formula (1) | 5 to 48 |
| surfactant or surfactant blend | 2 to 20% |
| Aromatic Solvent or Mixture | 55 to 75% |

We claim:

1. A compound of the formula (1)

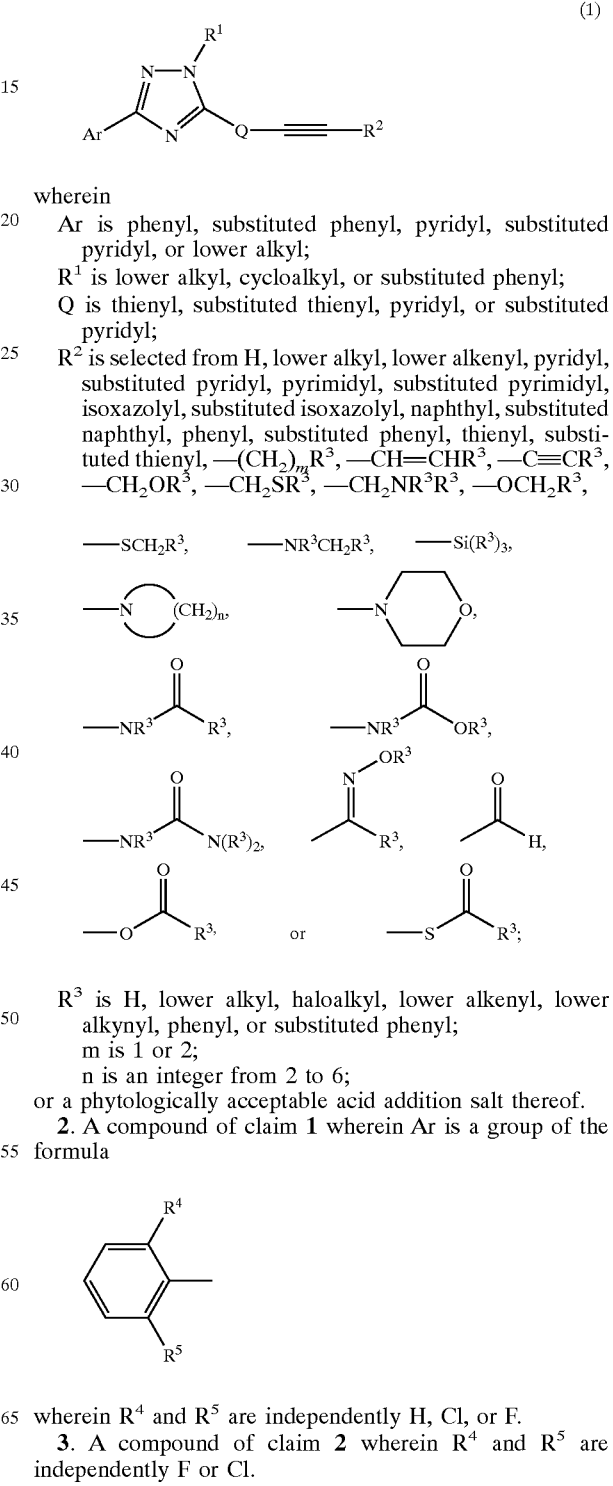

wherein
Ar is phenyl, substituted phenyl, pyridyl, substituted pyridyl, or lower alkyl;
$R^1$ is lower alkyl, cycloalkyl, or substituted phenyl;
Q is thienyl, substituted thienyl, pyridyl, or substituted pyridyl;
$R^2$ is selected from H, lower alkyl, lower alkenyl, pyridyl, substituted pyridyl, pyrimidyl, substituted pyrimidyl, isoxazolyl, substituted isoxazolyl, naphthyl, substituted naphthyl, phenyl, substituted phenyl, thienyl, substituted thienyl, —$(CH_2)_m R^3$, —$CH=CHR^3$, —$C\equiv CR^3$, —$CH_2OR^3$, —$CH_2SR^3$, —$CH_2NR^3R^3$, —$OCH_2R^3$, —$SCH_2R^3$, —$NR^3CH_2R^3$, —$Si(R^3)_3$, $R^3$ is H, lower alkyl, haloalkyl, lower alkenyl, lower alkynyl, phenyl, or substituted phenyl;
m is 1 or 2;
n is an integer from 2 to 6;
or a phytologically acceptable acid addition salt thereof.

2. A compound of claim 1 wherein Ar is a group of the formula wherein $R^4$ and $R^5$ are independently H, Cl, or F.

3. A compound of claim 2 wherein $R^4$ and $R^5$ are independently F or Cl.

4. A compound of claim 2 wherein $R^4$ and $R^5$ are both F.

5. A compound of claim 2 wherein $R^4$ is F and $R^5$ is Cl.

6. A compound of of claim 1 wherein Ar is a group of the formula

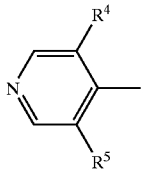

wherein $R^4$ and $R^5$ are independently H, Cl, or F.

7. A compound of claim 6 wherein $R^4$ and $R^5$ are independently F or Cl.

8. A compound of claim 2 wherein $R^4$ and $R^5$ are both Cl.

9. A compound of claim 1 wherein Ar is lower alkyl.

10. A compound of claim 1 wherein Q is a thiophene or substituted thiophene.

11. A Compound of claim 1 wherein Q is a pyridyl or substituted pyridyl.

12. A compound of claim 1 wherein $R^1$ is methyl, ethyl, hydrogen, cyclohexyl, or substituted phenyl.

13. A compound of claim 1 wherein $R^2$ is a phenyl or substituted phenyl.

14. A compound of claim 1 wherein $R^2$ is a thiophene or substituted thiophene.

15. A compound of claim 1 wherein $R^2$ is a trimethyl silyl, lower alkyl (ethyl, propyl, n-butyl, t-butyl), or lower alkenyl (propenyl).

16. A composition for controlling insects or mites which comprises a compound of claim 1 in combination with a phytologically-acceptable carrier.

17. A method of controlling insects or mites which comprises applying to a locus where control is desired an insect- or mite-inactivating amount of a compound of claim 1.

18. A method of controlling beet armyworm which comprises applying to a locus where control is desired a beet armyworm inactivating amount of a compound of claim 1.

19. A method of controlling tobacco budworm which comprises applying to a locus where control is desired a tobacco budworm inactivating amount of a compound of claim 1.

20. A method of controlling cabbage looper which comprises applying to a locus where control is desired a cabbage looper inactivating amount of a compound of claim 1.

21. A method of controlling aphids which comprises applying to a locus where control is desired an aphid inactivating amount of a compound of claim 1.

22. A method of controlling whitefly which comprises applying to a locus where control is desired a whitefly inactivating amount of a compound of claim 1.

23. A method of controlling mites which comprises applying to a locus where control is desired a mite-inactivating amount of a compound of claim 1.

24. A method of protecting a plant from aphids, mites, or insects which comprises treating plant seed prior to planting it, treating soil where plant seed is to be planted, or treating soil at the roots of a plant after it is planted, with an effective amount of a compound of claim 1.

25. A process for preparing a compound of formula (1)

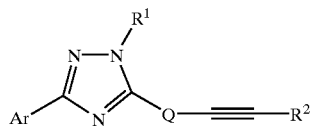

(1)

wherein

Ar is phenyl, substituted phenyl, pyridyl, substituted pyridyl, or lower alkyl;

$R^1$ is lower alkyl, cycloalkyl, or substituted phenyl;

Q is thienyl, substituted thienyl, pyridyl, or substituted pyridyl;

$R^2$ is selected from H, lower alkyl, lower alkenyl, pyridyl, substituted pyridyl, pyrimidyl, substituted pyrimidyl, isoxazolyl, substituted isoxazolyl, naphthyl, substituted naphthyl, phenyl, substituted phenyl, thienyl, substituted thienyl, —(CH$_2$)$_m$R$^3$, —CH=CHR$^3$, —C≡CR$^3$, —CH$_2$OR$^3$, —CH$_2$SR$^3$, —CH$_2$NR$^3$R$^3$, —OCH$_2$R$^3$, —SCH$_2$R$^3$, —NR$^3$CH$_2$R$^3$, —Si(R$^3$)$_3$,

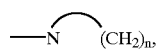 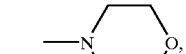

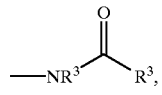 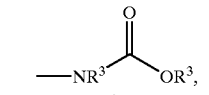

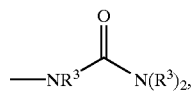 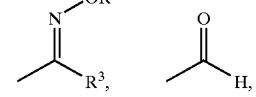

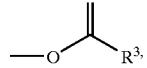 or 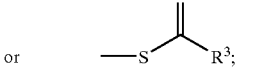

$R^3$ is H, lower alkyl, haloalkyl, lower alkenyl, lower alkynyl, phenyl, or substituted phenyl;

m is 1 or 2;

n is an integer from 2 to 6;

which comprises reacting a compound of formula

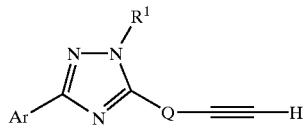

wherein Ar, Q, and $R^1$ are as defined above, with an appropriately substituted aryl iodide or aryl bromide of $R^2$ under palladium catalysis.

26. A process for preparing a compound of formula (1)

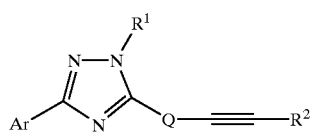

(1)

wherein

Ar is phenyl, substituted phenyl, pyridyl, substituted pyridyl, or lower alkyl;

R¹ is lower alkyl, cycloalkyl, or substituted phenyl;
Q is thienyl, substituted thienyl, pyridyl, or substituted pyridyl;
R² is selected from H, lower alkyl, lower alkenyl, pyridyl, substituted pyridyl, pyrimidyl, substituted pyrimidyl, isoxazolyl, substituted isoxazolyl, naphthyl, substituted naphthyl, phenyl, substituted phenyl, thienyl, substituted thienyl, —(CH$_2$)$_m$R³, —CH=CHR³, —C≡CR³, —CH$_2$OR³, —CH$_2$SR³, —CH$_2$NR³R³, —OCH$_2$R³, —SCH$_2$R³, —NR³CH2R³, —Si(R³)$_3$,

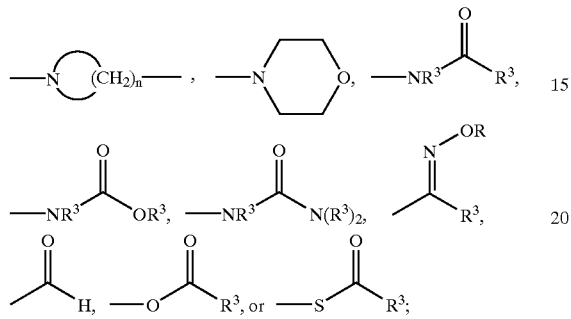

R³ is H, lower alkyl, haloalkyl, lower alkenyl, lower alkynyl, phenyl, or substituted phenyl;
m is 1 or 2;
n is an integer from 2 to 6;;

which comprises reacting a compound of formula

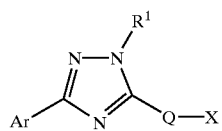

wherein Ar, Q, and R¹ are as defined above, and X is Br or I with a terminal alkyne of R² of formula (1) in claim 1 under palladium catalysis.

27. A compound of the formula

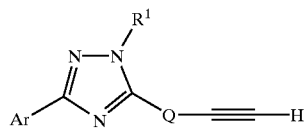

wherein
Ar is phenyl, substituted phenyl, pyridyl, substituted pyridyl, or lower alkyl;
R¹ is lower alkyl, cycloalkyl, or substituted phenyl;
Q is thienyl, substituted thienyl, pyridyl, or substituted pyridyl.

* * * * *